US00PP27307P2

(12) United States Plant Patent
Johnson, Jr.

(10) Patent No.: US PP27,307 P2
(45) Date of Patent: Oct. 25, 2016

(54) ***BEGONIA* PLANT NAMED 'FLIRTY GIRL'**

(50) Latin Name: ***Begonia* hybrid**
Varietal Denomination: Flirty Girl

(71) Applicant: Ozzie W. Johnson, Jr., Marietta, GA (US)

(72) Inventor: Ozzie W. Johnson, Jr., Marietta, GA (US)

(73) Assignee: ITSAUL PLANTS, LLC, Alpharetta, GA (US)

( * ) Notice: Subject to any disclaimer, the term of this patent is extended or adjusted under 35 U.S.C. 154(b) by 0 days.

(21) Appl. No.: 14/545,722

(22) Filed: Jun. 10, 2015

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238
See application file for complete search history.

*Primary Examiner* — Kent L Bell
(74) *Attorney, Agent, or Firm* — Penny J. Aguirre

(57) ABSTRACT

A new cultivar of *Begonia* of hybrid origin named 'Flirty Girl', that is characterized by its mallet-type cane plant habit with cane branching, thin colorful foliage and an intermediate plant size, its dense vertical basal branching, its pendant flowers that are pink in color; female flowers exhibit prominent winged ovaries that are deep pink in color and persist until seed ripening and male flowers are held flat and persist less than one day, its very long bloom period that is ever-blooming when greenhouse grown, and its colorful foliage with the upper surface emerging silver-green with dark green margins and main veins and develops a rosy blush when mature and a lower surface that is bright green with red margins and veins.

2 Drawing Sheets

Botanical classification: *Begonia* hybrid.
Cultivar designation: 'Flirty Girl'.

BACKGROUND OF THE INVENTION

The present invention relates to a new and distinct cultivar of *Begonia* plant of hybrid origin, botanically known as *Begonia* 'Flirty Girl' and will be referred to hereafter by its cultivar name, 'Flirty Girl'.

'Flirty Girl' was derived from a breeding program conducted by the Inventor in Marietta, Ga., USA. The objectives of the breeding program were to develop new cultivars of *Begonia* with long bloom seasons, increased cold hardiness, and colorful foliage. 'Flirty Girl' originated as a seedling that arose from seed planted from open pollination of 'Georgia Tasker' (not patented) in summer of 2010. The exact male parentage is unknown, however the likely male parent is an unnamed and unpatented plant of *Begonia acetosella* based on the observed stem structure, leaf shape, and its proximity to the seed parent. 'Flirty Girl' was selected as a single unique plant in summer of 2011 from amongst the resulting seedlings.

Asexual propagation of the new cultivar was first accomplished by the Inventor by stem cuttings in Marietta, Ga. in July of 2012. Asexual propagation by stem cuttings and in vitro propagation has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Flirty Girl' as a new and distinct cultivar of *Begonia*.

1. 'Flirty Girl' exhibits a mallet-type cane plant habit with cane branching, thin colorful foliage and an intermediate plant size.
2. 'Flirty Girl' exhibits pendant flowers that are pink in color; female flowers exhibit prominent winged ovaries that are deep pink in color and persist until seed ripening and male flowers are held flat and persist less than one day.
3. 'Flirty Girl' exhibits a very long bloom period and is ever blooming when greenhouse grown.
4. 'Flirty Girl' exhibits dense vertical basal branching from its base that forms a low mound that later develops elongated canes.
5. 'Flirty Girl' exhibits colorful foliage with the upper surface emerging silver-green with dark green margins and main veins and develops a rosy blush when mature and a lower surface that is bright green with red margins and veins.

The female parent of 'Flirty Girl', 'Georgia Tasker', differs from 'Flirty Girl' in being a rhizomatous type *Begonia*, in being shorter in height, in having leaves that are larger, pubescent, and darker in color, and in having a shorter bloom season. The likely male parent of 'Flirty Girl' is similar to 'Flirty Girl' in leaf shape and surface and in having cane-type stems. The likely male parent of 'Flirty Girl' differs from 'Flirty Girl' in being much taller in height, in having leaves that are solid green in color, in having white flowers, and in having a very short bloom season. 'Flirty Girl' can be most closely compared to the *Begonia* cultivars 'Benigo' (not patented) and 'Sinbad' (not patented). 'Benigo' is similar to 'Flirty Girl' in having flowers that are pink in color and in having cane-type stems. 'Benigo' differs from 'Flirty Girl' in having foliage that is bronzed red on the lower surface and deep green and covered with raised silver and pink spots on the upper surface, in having foliage that emerges bronze in color, and in having fruit with equal length wings that run the length of the pod. 'Sinbad' is similar to 'Flirty Girl' in having foliage that is silver in color and in having a similar plant habit. 'Sinbad' differs from 'Flirty Girl' in having foliage that emerges pinkish-bronze in color and matures to a light green color that is covered with closely spaced silver dots and a red eye above the petiole attachment, in having stems that are red in color, and in having fruit with wings that run the length of the pod.

BRIEF DESCRIPTION OF THE DRAWING

The accompanying colored photograph illustrates the overall appearance and distinct characteristics of the new *Begonia*. The photograph was taken of a plant six months in age as grown in a one-gallon container under greenhouse conditions under filtered light in Alpharetta, Ga.

The photograph in FIG. 1 provides a side view of a plant of 'Flirty Girl' in bloom and illustrates its plant habit and foliage color with shade and cooler temperature.

Figure 1:
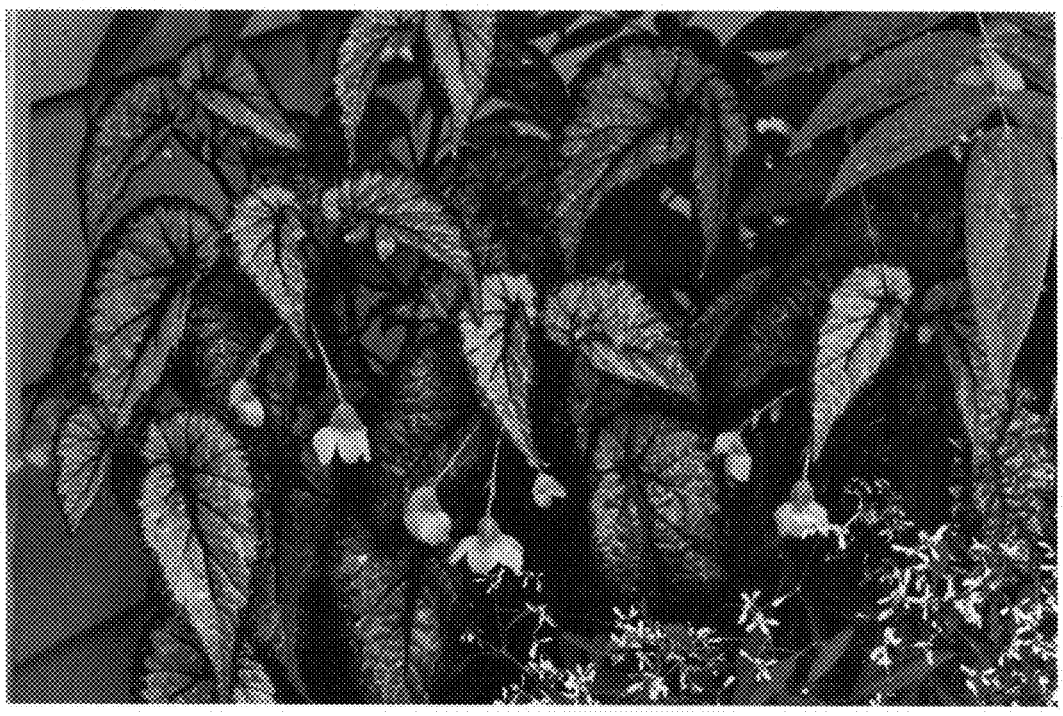
Figure 2:
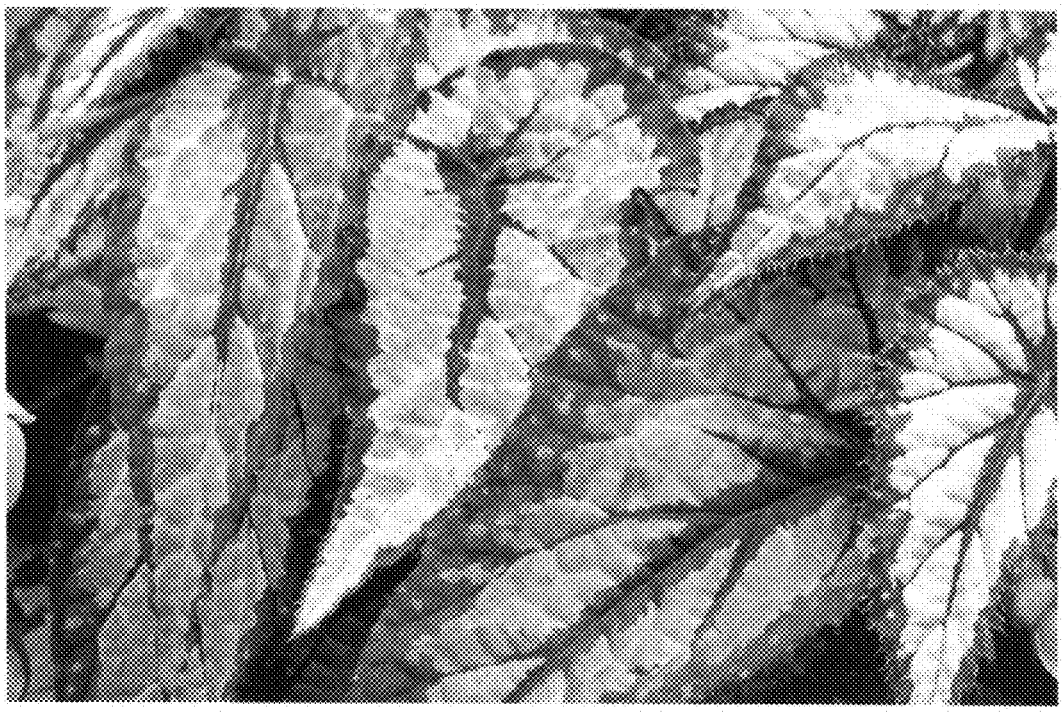

The photograph in FIG. 2 provides a view of the foliage coloration of the young and maturing foliage in higher light.

Figure 3:
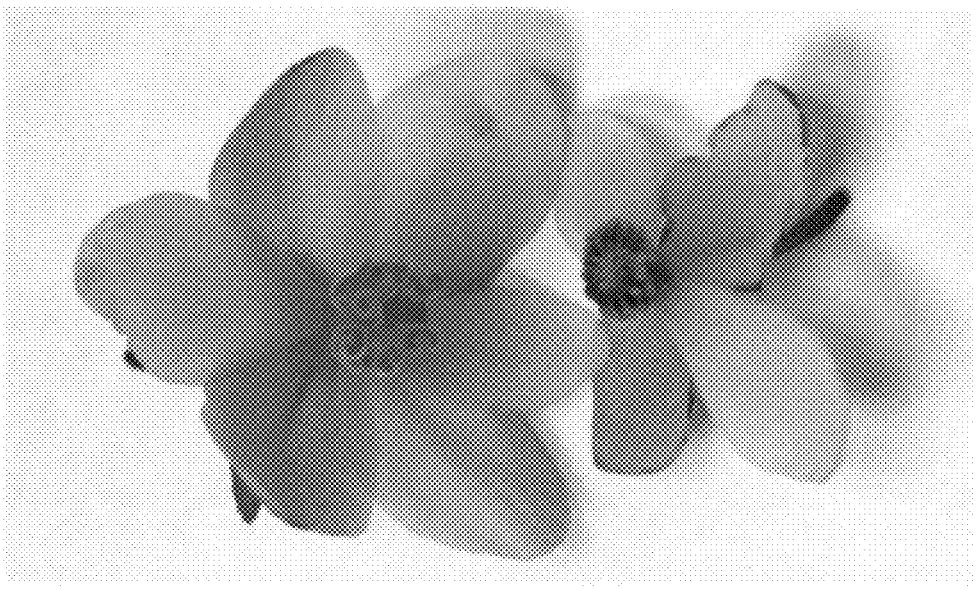

The photograph in FIG. 3 provides a view of the upper surface of a female flower (left) and male flower (right).

Figure 4:
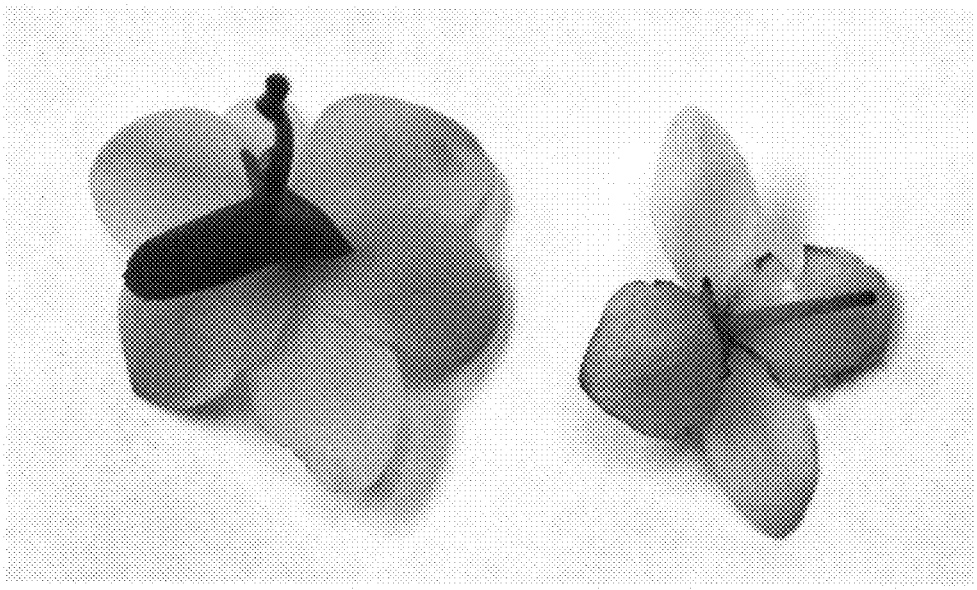

The photograh in FIG. 4 provides a view of the lower surface of a female flower (left) and male flower (right).

The colors in the photographs are as close as possible with the digital photography techniques available, the color values cited in the detailed botanical description accurately describe the colors of the new *Begonia*.

DETAILED BOTANICAL DESCRIPTION OF THE PLANT

The following is a detailed description of plants of the new cultivar six months in age as grown in one-gallon containers under greenhouse conditions with filtered shade in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming habit.*—Long blooming; blooming year around when growing in a greenhouse.

*Plant type.*—Deciduous perennial in tropical climate.

*Plant habit.*—Mallet-type canes, dense vertical basal branching from its base that forms a low mound that later develops elongated canes.

*Height and spread.*—Reaches about 38 cm in height and 30 cm in spread as grown in a one-gallon container.

*Cold hardiness.*—U.S.D.A. Zone 10; grown as an annual or as a greenhouse plant.

*Cultural conditions.*—Moderate to heavy fertilizer is required to maintain quality foliage and flowers.

*Diseases and pests.*—No susceptibility and resistance to diseases or pests as been observed.

*Root description.*—Fibrous, 200C in color.

*Growth rate.*—Moderate.

*Propagation.*—In vitro propagation (preferred) and stem cuttings.

*Root initiation.*—Soft tip cuttings initiate roots in 3 weeks in early spring and in 5 weeks in late fall/winter.

*Root development.*—Rooted cutting will fully develop in 3 to 5 weeks in 4 to 5 cm containers.

Stem description:

*Branching habit.*—Dense vertical basal branching from its base that forms a low mound that later develops elongated canes.

*Stem size.*—Up to 25 cm in length and 4.5 cm in width.

*Stem shape.*—Oval.

*Stem color.*—A color between 177A and 183A.

*Stem surface.*—Very sparsely pubescence with lenticels; 177D in color, an average of 12 per stem surface 3 cm in length and 4.5 mm in width, 0.5 mm in width and 1.2 mm in length.

*Internode length.*—Average of 3 cm.

Foliage description:

*Leaf shape.*—Broadly lanceolate with asymmetric base.

*Leaf division.*—Single.

*Leaf base.*—Irregularly cordate.

*Leaf apex.*—Acuminate.

*Leaf venation.*—Main veins are irregularly pinnate and conspicuous on both surfaces, upper surface; 147A on young leaves and N189A on mature leaves, lower surface; sparsely hairy, 187B on young and mature leaves.

*Leaf margins.*—Shallow crenate, wavy, short stiff hairs on tips of crenations of young leaves; 1 mm in length and about NN155A in color.

*Leaf attachment.*—Petiolate.

*Leaf arrangement.*—Alternate.

*Leaf surface.*—Upper surface; satiny, young leaves; moderately mottled with a silvery shine (due to dense short tomentose hairs) with a few random hairs about 1 mm in length and about NN155A in color, mature leaves; glossy with a heavy silver shine in the mottled regions, lower surface young and mature; dull and glabrous.

*Leaf color.*—Young leaves upper surface; main veins 147A, margins 147A and 147A blended with 200A on the very edge, central area a blend of 189A, 189B and 189C, young leaves lower surface; main veins, areas surrounding to veins and margins 187A, central areas 138B, mature leaves upper surface; main veins and margins N137A, central area a blend of N137A and 187B, mature leaves lower surface; main veins, areas surrounding to veins and margins 187A, central areas 138B.

*Leaf size.*—Up to 15 cm in length and 7 cm in width when mature.

*Leaf quantity.*—Average of 7 per stem.

*Leaf fragrance.*—None.

*Petioles.*—Young leaves; an average of 4 cm in length and 3 mm in width and a blend of 147B and 187B, surface is glossy and densely covered with stiff thorn like hairs at the base of the leaf and very slightly covering the remaining surface, hair length is an average of 2 mm and about 155C in color, mature leaves; an average of 7 cm in length and 5 mm in width and a blend of 146A and 187A and 183A, surface is glossy and slightly covered with stiff thorn like hairs; an average of 2 mm and about 155C in color.

*Stipules.*—None observed.

Flower description:

*Inflorescence type.*—Typically one male flower with an average of 3 female flowers below (cyme).

*Inflorescence size.*—Ranges with flower opening, typically 1 to 2 flowers open at a time, average of 5 cm in depth and 4 cm in diameter.

*Peduncles.*—Up to 4.5 cm in length and 2 to 3 mm in width (widest at base), color; 177A and slightly suffused with 146B, surface is primarily glabrous with a few sparse hairs.

*Flower persistence.*—Tepals self-cleaning with wing of ovary and stigmas persistent.

*Flower type.*—Single.

*Flower fragrance.*—Very slight.

*Flower number.*—Average of 6 flowers per stem present at one time.

*Flower aspect.*—Nodding.

*Bracts.*—2, present at base of peduncle, triangular in shape, aristate apex (awn about 2.5 mm in length), truncate base, about 8 mm in length and width, translucent and 61A in color (drying to 200C and 200D), waxy texture on upper and lower surface.

Male flowers:

*Pedicels.*—About 1.4 cm in length and 2 mm in width, color N77B, glabrous surface.

*Flower buds.*—Heart-shaped, about 1.4 cm in length and 1.2 cm in width, a blend of 63C and 63D in color.

*Flower size.*—About 3.6 cm in diameter and 8 mm in depth (including stamens).

*Tepals.*—4 in number (2 inner and 2 outer), outer tepals: broadly ovate in shape, rounded apex, rounded base, slightly cupped upward, average of 1.8 cm in length and 1.2 cm in width, glabrous on upper and lower surface, primarily entire margin, color inner and outer surface; a blend of 63B, 63C, and 63D in color, inner tepals: elliptic in shape, held flat, broadly acute apex, cuneate base, average of 1.5 cm in length and 1.2 cm in width, glabrous on upper and lower surface, entire margin, color on both surfaces a blend of 63C and 63D in color.

*Corolla form.*—Spreading outward, tepals are un-fused.

*Flower lastingness.*—A few hours.

*Stamens.*—Average of 80, formed into a globose cluster about 5 mm in diameter and and height, filament is very fine, 1.5 mm in length, and 145C in color, anther is about 3 mm in length and 1.5 mm in width, 10C in color when fresh, thick and petal-like and lanceolate in shape with an acute apex and truncate base at filament attachment, pollen is sparse and 158D in color.

Female flowers:

*Pedicels.*—Up to 1.5 cm in length and 1.5 mm in width, color N77B, glabrous surface.

*Flower buds.*—Closed campanulate in shape above a winged ovary, average of 2 cm in depth and 1 cm in diameter, a blend of 63B and 63C in color.

*Flower size.*—An average of 3 cm in depth and 2.5 cm in diameter.

*Flower lastingness.*—About 4 days after opening.

*Tepals.*—6 in number (3 inner and 3 outer), outer tepals; elliptic in shape, broadly acute apex, cuneate base, average of 1.9 cm in length and 1.2 cm in width, glabrous on both surfaces, entire margin, color inner and outer surface; a blend of 63B, 63C, and 63D in color, inner tepals; broadly to slightly obovate in shape, acute to broadly acute apex, cuneate base, average of 1.8 cm in length and 1.1 cm in width, glabrous on both surfaces, entire margin, color inner and outer surface; a blend of 63B, 63C, and 63D in color.

*Corolla form.*—Spreading, held slightly upward, tepals are un-fused.

*Styles.*—1 in number, cylindrical, stout, about 3 mm in length and 2 mm width, a blend of 145C and 63C in color.

*Stigmas.*—Crested (about 5 segments) and curly with short hairs, 8 mm in width and 3 mm in depth, 7B in color with hairs on margins 145B in color.

*Ovaries.*—Inferior, elliptic in shape, about 1.1 cm in length and 1 cm in width with wing 1.2 cm in length and 1 cm in width, a blend of 63B, 63C, and 63D in color becoming 63B in color and then 178A as the flower ages.

*Mature fruit.*—An average of 8 mm in length and 5 mm in width with dried wing 1 cm in length and 0.7 cm in width, color a blend of 200B to 200D, stigma is persistent, hundreds of oblong dust-like seeds (a fraction of a millimeter) pack the lower lobes of the fruit, color 164A.

It is claimed:

1. A new and distinct cultivar of *Begonia* plant named 'Flirty Girl' as herein illustrated and described.

* * * * *